(12) United States Patent
Shao et al.

(10) Patent No.: US 8,680,016 B2
(45) Date of Patent: Mar. 25, 2014

(54) TESTING METHOD OF NUCLEIC ACID BINDING PROTEIN BASED ON BIOCHIP

(75) Inventors: Wei Shao, Beijing (CN); Yongchao Zhao, Beijing (CN); Yimin Sun, Beijing (CN); Jiying Qiao, Beijing (CN); Huajiang Wei, Beijing (CN); Weiping Yang, Beijing (CN); Yuxiang Zhou, Beijing (CN); Jing Cheng, Beijing (CN)

(73) Assignees: CapitalBio Corporation, Beijing (CN); Tsinghua University, Beijing (CN)

( * ) Notice: Subject to any disclaimer, the term of this patent is extended or adjusted under 35 U.S.C. 154(b) by 718 days.

(21) Appl. No.: 11/791,157

(22) PCT Filed: Nov. 23, 2004

(86) PCT No.: PCT/CN2004/001340
§ 371 (c)(1),
(2), (4) Date: Nov. 28, 2007

(87) PCT Pub. No.: WO2006/053463
PCT Pub. Date: May 26, 2006

(65) Prior Publication Data
US 2009/0018025 A1    Jan. 15, 2009

(30) Foreign Application Priority Data
Nov. 18, 2004 (CN) .......................... 2004 1 0090423

(51) Int. Cl.
*C40B 20/02* (2006.01)
(52) U.S. Cl.
USPC ............................................................ 506/3
(58) Field of Classification Search
None
See application file for complete search history.

(56) References Cited

U.S. PATENT DOCUMENTS

| | | | |
|---|---|---|---|
| 5,449,603 A * | 9/1995 | Nielson et al. ..................... | 435/6 |
| 2003/0054378 A1 | 3/2003 | Karube et al. | |
| 2003/0215821 A1 * | 11/2003 | Gunderson et al. ............... | 435/6 |
| 2004/0115794 A1 | 6/2004 | Brubaker | |

FOREIGN PATENT DOCUMENTS

| CN | 1435492 A | 8/2003 |
|---|---|---|
| WO | WO-93/15226 A1 | 8/1993 |

(Continued)

OTHER PUBLICATIONS

Bae (Nature Biotechnology 2003 vol. 21 p. 275).*
Glover (Sep. 4, 1998) Journal of Biological Chemistry vol. 273 pp. 23476 to 23484.*

(Continued)

*Primary Examiner* — Christian Boesen
(74) *Attorney, Agent, or Firm* — Morrison & Foerster LLP

(57) ABSTRACT

A testing method of nucleic acid binding protein based on biochip, comprises the following steps: 1. puts a plurality of groups solution including nucleic acid captured probes into biological sample including a plurality of nucleic acid binding protein to be test, and thus forming nucleic acid captured probe-nucleic acid binding protein complexes; such nucleic acid captured probe includes at least a segment of binding sequence which can bind with aimed nucleic acid binding protein; 2. separates such nucleic acid captured probe-nucleic acid binding protein complexes, then recoveries nucleic acid captured probes; 3. hybridizes the nucleic acid captured probes according to step 2 with a plurality of single strand blotting probes on biochip substrate; the sequence of such blotting probe compensates with such nucleic acid captured probe or one of its strand; 4. detects the result of hybridization.

25 Claims, 8 Drawing Sheets

(56) References Cited

FOREIGN PATENT DOCUMENTS

| | | | |
|---|---|---|---|
| WO | WO-02/052037 A2 | 7/2002 | |
| WO | WO 02/52037 A2 * | 7/2002 | ............... C12Q 1/68 |
| WO | WO-02/052037 A3 | 7/2002 | |
| WO | WO-02/083929 A2 | 10/2002 | |
| WO | WO-02/083929 A3 | 10/2002 | |
| WO | WO-02/086095 A2 | 10/2002 | |
| WO | WO-02/086095 A3 | 10/2002 | |
| WO | WO-2004/011606 A2 | 2/2004 | |
| WO | WO-2004/011606 A3 | 2/2004 | |
| WO | WO-2004/046387 A1 | 6/2004 | |

OTHER PUBLICATIONS

International Search Report mailed Aug. 18, 2005, for PCT Application No. PCT/CN2004/001340, filed Nov. 23, 2004, two pages (English translation, two pages.).

Supplementary European Search Report mailed Jul. 21, 2008, for EP Application No. 04797371.4 filed Nov. 23, 2004, two pages.

Andras et al., Molecular Biotechnology (2001) 19:29-44.

Sanchez et al., PNAS USA (2004) 101(7):1933-1938.

Office Action from European Patent Application No. 04 797 371.4-2402, mailed on Sep. 30, 2010.

* cited by examiner (1) capture probe (2) immobilization probe

(1) capture probe

(2) immobilization proble

SEQUENCE LISTING

```
<160> NUMBER OF SEQ ID NOS: 28

<210> SEQ ID NO 1
<211> LENGTH: 45
<212> TYPE: DNA
<213> ORGANISM: Artificial Sequence
<220> FEATURE:
<223> OTHER INFORMATION: Synthetic construct

<400> SEQUENCE: 1
tttttttttt tttttttttt cgcttgatga gtcagccgga tcccg                45

<210> SEQ ID NO 2
<211> LENGTH: 25
<212> TYPE: DNA
<213> ORGANISM: Artificial Sequence
<220> FEATURE:
<223> OTHER INFORMATION: Synthetic construct

<400> SEQUENCE: 2
cgggatccgg ctgactcatc aagcg                                      25

<210> SEQ ID NO 3
<211> LENGTH: 20
<212> TYPE: DNA
<213> ORGANISM: Artificial Sequence
<220> FEATURE:
<223> OTHER INFORMATION: Synthetic construct

<400> SEQUENCE: 3
cgcttgatga gtcagccgga                                            20

<210> SEQ ID NO 4
<211> LENGTH: 20
<212> TYPE: DNA
<213> ORGANISM: Artificial Sequence
<220> FEATURE:
<223> OTHER INFORMATION: Synthetic construct

<400> SEQUENCE: 4
tccggctgac tcatcaagcg                                            20

<210> SEQ ID NO 5
<211> LENGTH: 47
<212> TYPE: DNA
<213> ORGANISM: Artificial Sequence
<220> FEATURE:
<223> OTHER INFORMATION: Synthetic construct

<400> SEQUENCE: 5
tttttttttt tttttttttt agttgagggg actttcccag gatcccg              47

<210> SEQ ID NO 6
<211> LENGTH: 27
<212> TYPE: DNA
<213> ORGANISM: Artificial Sequence
<220> FEATURE:
<223> OTHER INFORMATION: Synthetic construct

<400> SEQUENCE: 6
cgggatcctg ggaaagtccc ctcaact                                    27
```

```
<210> SEQ ID NO 7
<211> LENGTH: 22
<212> TYPE: DNA
<213> ORGANISM: Artificial Sequence
<220> FEATURE:
<223> OTHER INFORMATION: Synthetic construct

<400> SEQUENCE: 7
agttgagggg actttcccag ga                                              22

<210> SEQ ID NO 8
<211> LENGTH: 22
<212> TYPE: DNA
<213> ORGANISM: Artificial Sequence
<220> FEATURE:
<223> OTHER INFORMATION: Synthetic construct

<400> SEQUENCE: 8
tcctgggaaa gtcccctcaa ct                                              22

<210> SEQ ID NO 9
<211> LENGTH: 46
<212> TYPE: DNA
<213> ORGANISM: Artificial Sequence
<220> FEATURE:
<223> OTHER INFORMATION: Synthetic construct

<400> SEQUENCE: 9
tttttttttt tttttttttt aaagccccgc cccgatataa ttcccg                    46

<210> SEQ ID NO 10
<211> LENGTH: 26
<212> TYPE: DNA
<213> ORGANISM: Artificial Sequence
<220> FEATURE:
<223> OTHER INFORMATION: Synthetic construct

<400> SEQUENCE: 10
cgggaattat atcggggcgg ggcttt                                          26

<210> SEQ ID NO 11
<211> LENGTH: 21
<212> TYPE: DNA
<213> ORGANISM: Artificial Sequence
<220> FEATURE:
<223> OTHER INFORMATION: Synthetic construct

<400> SEQUENCE: 11
aaagccccgc cccgatataa t                                               21

<210> SEQ ID NO 12
<211> LENGTH: 21
<212> TYPE: DNA
<213> ORGANISM: Artificial Sequence
<220> FEATURE:
<223> OTHER INFORMATION: Synthetic construct

<400> SEQUENCE: 12
attatatcgg ggcggggctt t                                               21

<210> SEQ ID NO 13
<211> LENGTH: 51
<212> TYPE: DNA
<213> ORGANISM: Artificial Sequence
<220> FEATURE:
<223> OTHER INFORMATION: Synthetic construct

<400> SEQUENCE: 13
```
tttttttttt tttttttttt cgcctacctc attttatatg ctctgctccc g        51

<210> SEQ ID NO 14
<211> LENGTH: 31
<212> TYPE: DNA
<213> ORGANISM: Artificial Sequence
<220> FEATURE:
<223> OTHER INFORMATION: Synthetic construct

<400> SEQUENCE: 14
cgggagcaga gcatataaaa tgaggtaggc g                               31

<210> SEQ ID NO 15
<211> LENGTH: 26
<212> TYPE: DNA
<213> ORGANISM: Artificial Sequence
<220> FEATURE:
<223> OTHER INFORMATION: Synthetic construct

<400> SEQUENCE: 15
cgcctacctc attttatatg ctctgc                                     26

<210> SEQ ID NO 16
<211> LENGTH: 26
<212> TYPE: DNA
<213> ORGANISM: Artificial Sequence
<220> FEATURE:
<223> OTHER INFORMATION: Synthetic construct

<400> SEQUENCE: 16
gcagagcata taaaatgagg taggcg                                     26

<210> SEQ ID NO 17
<211> LENGTH: 50
<212> TYPE: DNA
<213> ORGANISM: Artificial Sequence
<220> FEATURE:
<223> OTHER INFORMATION: Synthetic construct

<400> SEQUENCE: 17
tttttttttt tttttttttt ctatgtggtg aactcctcct aaatatcccg           50

<210> SEQ ID NO 18
<211> LENGTH: 35
<212> TYPE: DNA
<213> ORGANISM: Artificial Sequence
<220> FEATURE:
<223> OTHER INFORMATION: Synthetic construct

<400> SEQUENCE: 18
cgggacggga tatttaggag gagttcacca catag                           35

<210> SEQ ID NO 19
<211> LENGTH: 25
<212> TYPE: DNA
<213> ORGANISM: Artificial Sequence
<220> FEATURE:
<223> OTHER INFORMATION: Synthetic construct

<400> SEQUENCE: 19
ctatgtggtg aactcctcct aaata                                      25

<210> SEQ ID NO 20
<211> LENGTH: 48
<212> TYPE: DNA
<213> ORGANISM: Artificial Sequence

```
<220> FEATURE:
<223> OTHER INFORMATION: Synthetic construct

<400> SEQUENCE: 20
tttttttttt tttttttttt agacggaaga catatggccg ctctcccg          48

<210> SEQ ID NO 21
<211> LENGTH: 28
<212> TYPE: DNA
<213> ORGANISM: Artificial Sequence
<220> FEATURE:
<223> OTHER INFORMATION: Synthetic construct

<400> SEQUENCE: 21
cgggagagcg gccatatgtc ttccgtct                                28

<210> SEQ ID NO 22
<211> LENGTH: 44
<212> TYPE: DNA
<213> ORGANISM: Artificial Sequence
<220> FEATURE:
<223> OTHER INFORMATION: Synthetic construct

<400> SEQUENCE: 22
cgcttgatga gtcagccgga ccctatagtg agtcgtatta cccc              44

<210> SEQ ID NO 23
<211> LENGTH: 46
<212> TYPE: DNA
<213> ORGANISM: Artificial Sequence
<220> FEATURE:
<223> OTHER INFORMATION: Synthetic construct

<400> SEQUENCE: 23
agttgagggg actttcccag gaccctatag tgagtcgtat taccccc           46

<210> SEQ ID NO 24
<211> LENGTH: 45
<212> TYPE: DNA
<213> ORGANISM: Artificial Sequence
<220> FEATURE:
<223> OTHER INFORMATION: Synthetic construct

<400> SEQUENCE: 24
aaagccccgc ccgatataa tccctatagt gagtcgtatt acccc              45

<210> SEQ ID NO 25
<211> LENGTH: 24
<212> TYPE: DNA
<213> ORGANISM: Artificial Sequence
<220> FEATURE:
<223> OTHER INFORMATION: Synthetic construct

<400> SEQUENCE: 25
ggggtaatac gactcactat aggg                                    24

<210> SEQ ID NO 26
<211> LENGTH: 25
<212> TYPE: DNA
<213> ORGANISM: Artificial Sequence
<220> FEATURE:
<223> OTHER INFORMATION: Synthetic construct

<400> SEQUENCE: 26
cgggatccgg ctgactcatc aagcg                                   25
```

```
<210> SEQ ID NO 27
<211> LENGTH: 27
<212> TYPE: DNA
<213> ORGANISM: Artificial Sequence
<220> FEATURE:
<223> OTHER INFORMATION: Synthetic construct

<400> SEQUENCE: 27
cgggatcctg ggaaagtccc ctcaact                                    27

<210> SEQ ID NO 28
<211> LENGTH: 26
<212> TYPE: DNA
<213> ORGANISM: Artificial Sequence
<220> FEATURE:
<223> OTHER INFORMATION: Synthetic construct

<400> SEQUENCE: 28
cgggaattat atcggggcgg ggcttt                                     26
```

TESTING METHOD OF NUCLEIC ACID BINDING PROTEIN BASED ON BIOCHIP

This application is a national stage of International Patent Application Serial No. PCT/CN2004/001340, filed Nov. 23, 2004, which claims the priority benefit of Chinese Application Serial No. 200410090423.3, filed Nov. 18, 2004.

TECHNICAL FIELD

This invention discloses methods for detecting nucleic acid binding proteins, especially a biochip-based method for detecting nucleic acid binding proteins.

BACKGROUND

Nucleic acid binding proteins include double-stranded DNA binding (dsDNA) proteins, single-stranded DNA (ssDNA) binding proteins and RNA binding proteins, etc.

dsDNA binding proteins are a group of proteins or protein molecule complexes which bind to specific sequences of dsDNA. dsDNA binding proteins include repressors and operator proteins of prokaryotes and transcription factors (TF) of eukaryotes, etc. These dsDNA binding proteins can activate, inhibit, reduce or enhance expression of target genes via binding to specific sequences of dsDNA (operator/promoter). In prokaryotes, the functions of repressor and operator proteins are relatively simple. They regulate genes encoding enzymes related to cellular metabolism and antibiotics resistance genes to adjust cellular physiological activity to the outside environment. In eukaryotes, transcription factors involve in many activities. Cell cycle, apoptosis, and tumorgenesis, etc., are all related to specific transcription factors. In biological system, especially in eukaryotic gene expression regulation network, expression of protein encoding genes includes: transcription activation via transcription factors, transcription, modification after transcription (splicing and 5' and 3' capping of RNA), translation, modification after translation (phosphorylation, glycosylation, acetylation, etc.), and is regulated at pre-transcriptional, post-transcriptional and post-translational levels.

Transcription activation via transcription factors is the first and important step in gene expression regulation network. Most of the stress reactions of an biological system to outside environment involve activation or turning off certain genes via specific transcription factors. Research indicates that expression of most of the eukaryotic genes is regulated by one or more specific transcription factors. More complicated organisms have more transcription factors and more complicated gene expression regulation mechanisms. As estimated, more than 5% protein encoding genes encode transcription factors. Many transcription factors are tightly related to cancers. For example, some transcription factors are only expressed in malignant tumors or can enhance expression of oncogenes (such as FOS and C-Myc); other transcription factors express weakly or do not express in malignant tumors (such as p53 and E2F). Thus, detecting levels of certain or all transcription factors in an organism at a certain time, combined with data of their target genes, allows obtaining regulation information before transcription. This information could be used for diagnosing tumorgenesis in a tissue, screening for drug target, studying mechanisms of cell stress responses, and observing activation and closing of cellular signal path, etc.

cDNA microarray technology is able to give mRNA profiling of all the transcription factor encoding genes of the genome. But only active transcription factors contribute to the regulation of gene expression. Activities of transcription factors usually are regulated by multiple protein modifications including phosphorylation, acetylation, glycosylation, etc. or intracellular localization of the transcription factors. Therefore, the quantities of active transcription factors do not always correlate with the quantities of transcription factors' in RNAs or proteins. For example, mRNA and protein expression level of the transcription factor Yin Yang 1 (YY1) are steady during cell cycle, but the level of the active YY1 changes greatly in different cell cycle stages. Thus, cDNA microarray technology cannot provide transcription factor expression information that researchers are interested in.

Conventional method for detecting "active" dsDNA binding protein is the gel shifting method (EMSA: Electrophoretic Mobility-Shift Assay, gel shift, band shift). Proteins to be tested are mixed with known dsDNA molecules labeled with radioisotopes. The reaction product is analyzed under polyacrylamide gel electrophoresis under non-denaturing condition. During electrophoresis, dsDNA molecules bound by proteins run slower than dsDNA molecules not bound by proteins. After electrophoresis, the result could be read by a autoradiography. On the film, separated electrophoresis bands could be seen and is used to detect binding between dsDNA and nucleic acid binding proteins. Recently, gel shifting technology has been improved. For example, fluorescence has been used to substitute radioisotopes. To solve nonspecific binding, antibody specific for dsDNA binding protein is used to detect DNA-protein complex. This method is called Super-shift. Gel shifting method has facilitated research in interaction between DNA and protein. However, it has obvious disadvantages: it involves complicated procedures; it is time and labor consuming (the experiment takes a whole day); it is low throughput (only one dsDNA binding protein is detected at a time); it requires large volume of sample if multiple dsDNA binding proteins are to be detected; it is hazardous to human if radioisotopes are used; and it is expensiveness if chemical or fluorescent dye is used.

Mercury™ transcription factor kit is a product from BD Biosciences Clontech Inc. (Palo Alto, Calif.). This kit provides a 96-well plate for detection of transcription factors. dsDNA probes which can be bound specifically by a transcription factor are immobilized onto the inner surface of each well. After a protein sample is added into the well, the immobilized dsDNA probes will bind to the corresponding transcription factors in the sample. After washing, primary antibody that specifically recognizes the transcription factor and enzyme-labeled secondary antibody which specifically recognizes the primary antibody are added one by one. Chemical dye is used for assay detection. This method is faster than the traditional EMSA method, and chemical dye is used instead of bio-hazardous radioisotopes. But this method is still a low-throughput method, and only one transcription factor could be examined at any one time in one well. Large volume of sample is needed for detecting multiple dsDNA binding proteins. There is a need for transcription factor specific antibodies and most of the transcription factor antibodies are not commercially available.

There are some sequence-specific ssDNA binding proteins and RNA binding proteins which regulate physiological activities in biological systems. More and more "antibody-like" aptamers which can specifically bind to target protein molecules are acquired by in vitro evolution method in recent years. There are no high-throughput methods for detecting these nucleic acid binding proteins.

DISCLOSURE OF THE INVENTION

The object of the present invention is to provide a biochip-based, high-throughput, sensitive and specific method for detecting nucleic acid binding proteins.

The invention provides a biochip-based method of detecting nucleic acid binding proteins, comprising the following steps: 1) adding a solution containing several groups of nucleic acid capture probes to a biological sample containing target nucleic acid binding proteins, whereby complexes between the nucleic acid capture probes and the nucleic acid binding proteins are formed, wherein the nucleic acid capture probes contain at least a sequence that target nucleic acid binding proteins can bind; 2) isolating the nucleic acid capture probe-nucleic acid binding protein complexes and collecting the nucleic acid capture probes in the complexes; 3) hybridizing the collected capture probes in step 2) with single stranded immobilization probes immobilized on the substrate of a biochip, wherein the immobilization probes contain a sequence complementary to the corresponding nucleic acid capture probes or one strand of the nucleic acid capture probes; and 4) detecting hybridization result.

In some embodiments, the isolation of the nucleic acid capture probe-nucleic acid binding protein complexes in step 2) may be performed using any of the five process described below: a) gel electrophoresis of the mixture from step 1), cutting gel slices, and recovering with gel purification kit or electro-elution method to obtain the isolated nucleic acid capture probe-nucleic acid binding protein complexes; b) chromatographying the mixture from step 1) to obtain the isolated nucleic acid capture probe-nucleic acid binding protein complexes; c) filtering the mixture from step 1) with a membrane capable of adsorbing proteins to obtain the isolated nucleic acid capture probe-nucleic acid binding protein complexes; d) adding antibodies specifically recognizing each nucleic acid binding protein to the mixture from step 1) and isolating via antibody purification method (for example, using protein A/G coated agarose beads to bind antibodies) to obtain the isolated nucleic acid capture probe-nucleic acid binding protein complexes; and e) separating the mixture from step 1) by capillary electrophoresis device and automatically collecting the nucleic acid capture probe-nucleic acid binding protein complexes.

In some embodiments, the invention (named "end-label method") is used to detect nucleic acid binding proteins, for example dsDNA binding proteins, ssDNA binding proteins, RNA binding proteins (such as HuB, HuC, ELAV, etc.), non-natural protein binding nucleic acid aptamers developed by in vitro evolution (such as thrombin aptamer).

Preferably, the nucleic acid binding proteins are dsDNA binding proteins; more preferably, are transcription factors, such as AP1, Sp1, p53, E2F, etc.

In a preferred embodiment for detection using the method of the present invention, said nucleic acid capture probes comprise a nucleic acid sequence which can bind to a target nucleic acid binding protein; and one strand of each nucleic acid capture probes has an overhang.

In order to enhance hybridization affinity between the nucleic acid capture probes and the immobilization probes, said immobilization probes are completely complementary to the overhang sequence of the corresponding nucleic acid capture probes.

In order to detect the hybridization signal, the overhang of the nucleic acid capture probes is labeled with a labeling molecule. The preferred labeling molecules are biotin, digoxin, fluorescent dyes, quantum dots, gold particles or nano-particles.

In order to reach the higher sensitivity, improvement is made as following ("pre-hybridization single strand amplification method"): one strand of each said nucleic acid capture probes has a 3' overhang; before the hybridization reaction in step 3), the collected nucleic acid capture probes are amplified using one primer whose sequence can hybridize with the 3' overhang sequence for later nucleic acid amplification procedures.

Preferably, the 3' overhang sequence in each nucleic acid capture probes is identical, and the primer sequence is completely complementary to the 3' overhang sequence.

To conveniently detect hybridization signals, labeling molecules may be added into the system. The primer may be end-labeled before amplification; or labeled nucleotides, added into the amplification materials, may be used during amplification. The preferred labeling molecules are biotin, digoxin, fluorescent dyes, quantum dots, gold particles or nano-particles.

In order to reach the higher sensitivity, improvement is made as following ("pre-hybridization double-strand amplification method"): one strand of each said nucleic acid capture probes has both a 3' overhang and a 5' overhang; before hybridization reaction in step 3), the collected nucleic acid capture probes are amplified using two primers in which one primer can hybridize with the 3' overhang of the strand of the nucleic acid capture probes having both the 3' overhang and the 5' overhang, and the other primer sequence is the same as the 5' overhang of the strand of the nucleic acid capture probes having both the 3' overhang and the 5' overhang.

Preferably, the 3' overhang sequence in each nucleic acid capture probes having both the 3' overhang and the 5' overhang is identical, and the 5' overhang sequence in each nucleic acid capture probes having both the 3' overhang and the 5' overhang is identical; and one primer sequence used can hybridize with the 3' overhang sequence of the nucleic acid capture probes having both the 3' overhang and the 5' overhang, and the other primer sequence is the same as the 5' overhang of the nucleic acid capture probes having both the 3' overhang and the 5' overhang.

The operation procedures of the double-strand amplification method is shown in FIG. 7. Capture probes 1 and target proteins 3 (represented by the circle and the triangle in the figure) are mixed; nucleic acid capture probe-nucleic acid binding protein complexes 4 are isolated and capture probes in the complexes are collected; two primers 6 are used to amplify the collected capture probes; the amplified products are hybridized with immobilization probes 2 immobilized on the biochip; and the hybridization signal is detected to obtain the results. The preferred design for capture probes, immobilization probes, and the primers is shown in FIG. 8: the capture probes contain a target protein binding sequence; one strand of the two strands has a 3' overhang and a 5' overhang; primer 1 sequence is complementary to the 3' overhang, and primer 2 sequence is the same as the 5' overhang; and the sequence of the immobilization probe is the same as the binding sequence.

To conveniently detect hybridization signals, labeling molecules may added into the system. The primer may be end-labeled before amplification; or labeled nucleotides, added into the amplification materials may be used during amplification. The preferred labeling molecules are biotin, digoxin, fluorescent dyes, quantum dots, gold particles or nano-particles.

BRIEF DESCRIPTIONS OF THE FIGURES

PREFERRED EMBODIMENTS

Example 1

Using DNA biochip to simultaneously detect three nucleic acid binding proteins AP1, NFkB and Sp1 (end labeling method)

Figure 1:
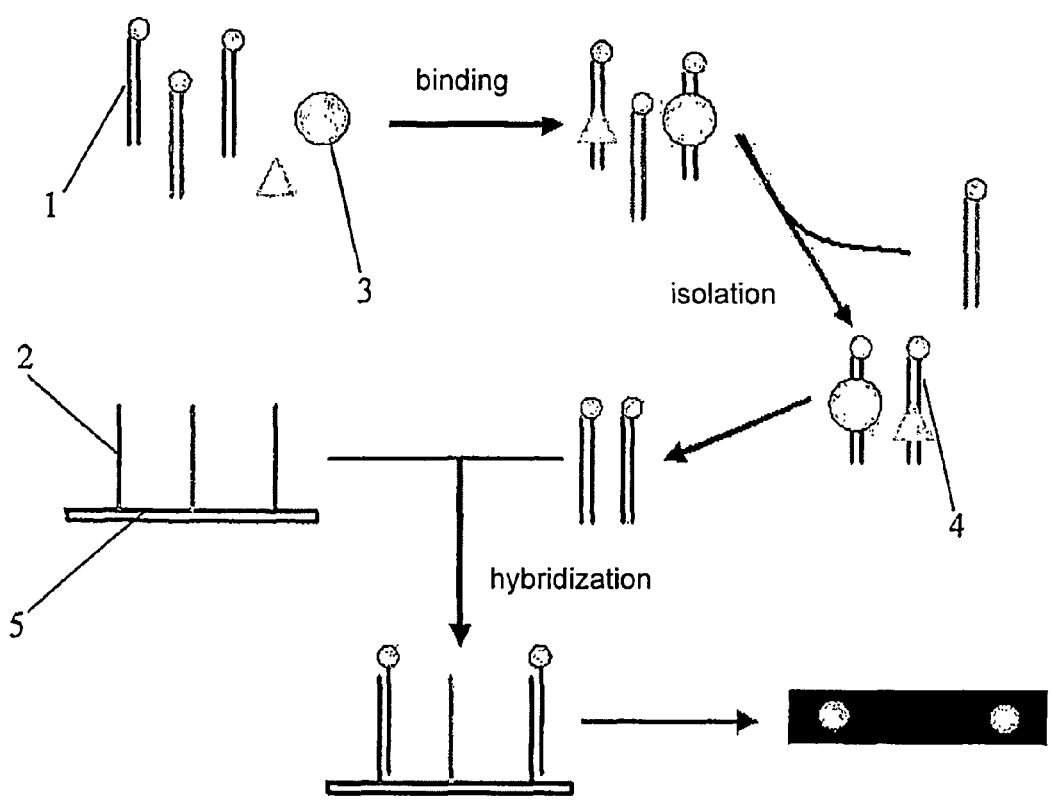
FIG. 1 shows a diagram of detection of multiple nucleic acid binding proteins with "end labeling method" used in the present invention.

As shown in FIG. 1, the end labeled capture probes 1 were mixed with target proteins 3 (represented by the circle and the triangle in the Figure). The nucleic acid capture probe-nucleic acid binding protein complexes 4 formed were then isolated and the capture probes in the complexes were collected. The collected capture probes were hybridized with immobilization probes 2 immobilized on a biochip 5, and the hybridization signal was detected to obtain the result.

Figure 2:
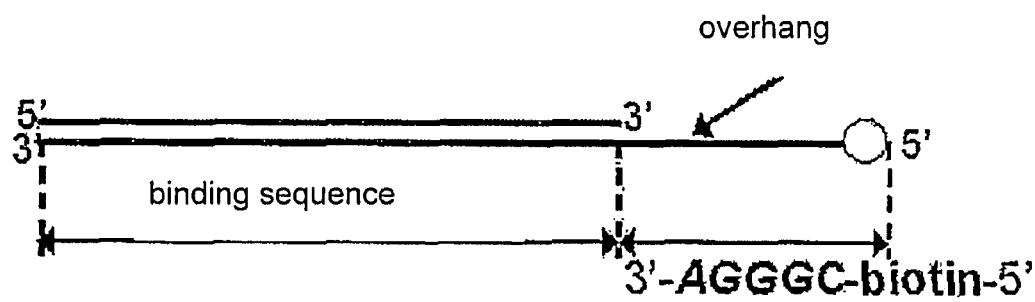
FIG. 2 shows a diagram of probe structures for detection of multiple nucleic acid binding proteins with "end labeling method" used in the present invention.
Figure 2:
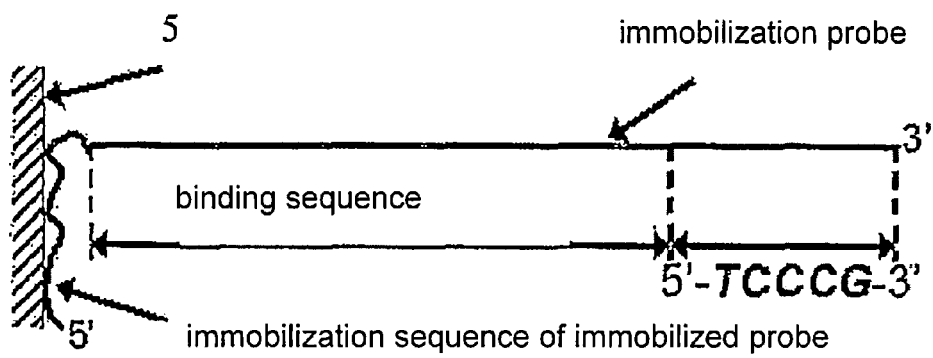

FIG. 2 shows a preferred design for capture probes and immobilized probes. The double stranded capture probe contains a sequence that a target nucleic acid binding protein binds. One strand in the capture probe contains an overhang which is labeled with a labeling molecule, a biotin in the Figure. The immobilization probe is complementary to the longer strand of the capture probe.

Materials:

The transcription factor AP-1(c-Jun) (#E3061), NFkB (p50) (#E3770) and Sp1 (#E6391) were obtained from Promega (Madison, Wis.). The general binding buffer contained 10 mM Tris-HCl (pH 7.5), 4% glycerol, 1 mM MgCl2, 0.5 mM EDTA, 5 mM DTT, 50 mM NaCl, and 0.05 mg/mL poly (dl-dC)·(dl-dC). The electrophoresis buffer was 0.5× TBE (0.9 M Tris, 0.9 M boric acid, 0.02 M EDTA, pH 8.0). PBST (PBS, 0.1% Tween 20) was used as washing buffer. The agarose for electrophoresis was obtained from Biowest (Miami, Fla.). Bovine serum albumin (BSA) was obtained from Amresco (Solon, Ohio). The Cy3-labeled streptavidin was obtained from Amersham Biosciences (Uppsala, Sweden).

Experimental Procedures:

A. Preparation of DNA probes: All the probes were synthesized by Bioasia Inc. (Shanghai, China) and their sequences are listed in Table 1. In Table 1, AP-1-IP represented the immobilization probe for AP-1; AP-1-LP and AP-1-FP formed the capture probe for AP1; and AP-1-CP and AP-1-FP formed the competitor probe for AP-1 binding. The designation of other probes was similar to those of AP-1. The sequence of the overhang of the LP probe in this example was 5'-CGGGA-3'. The immobilization probes for each group were first dissolved in water and then diluted with 50% DMSO aqueous solution to make the final probe concentration of 10 μM. The protein capture probes were dissolved in water, and were allowed to anneal with corresponding probes (FP and LP in each capture probe group) from the same group respectively to form double stranded DNA molecules. Each double stranded DNA molecule had a final concentration of 60 nM.

Figures 3A, 3B, 3C:
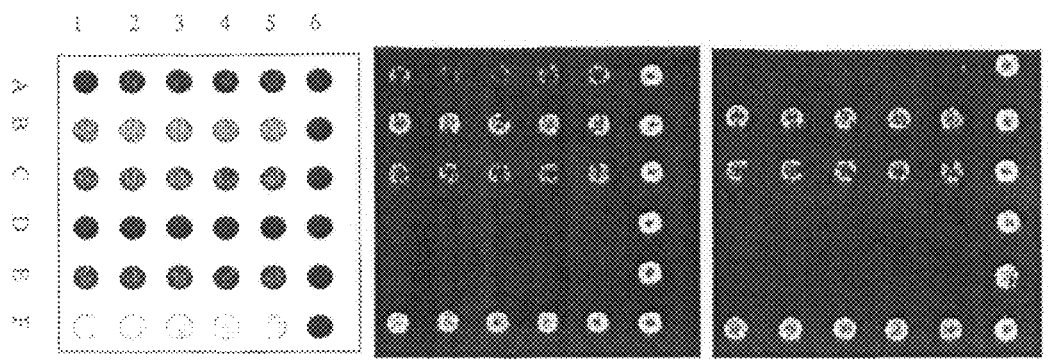
FIG. 3A shows an array format used in Example 1.
FIG. 3B shows the experimental results of simultaneous detection of three nucleic acid binding proteins in Example 1.
FIG. 3C shows the experimental results of simultaneous detection of three nucleic acid binding proteins in Example 1, in which a competitor AP1 binding probe was added.

B. Preparation of DNA chip: PixSys5500 Robotic Arrayer (Cartesian Technologies, Irvine, Calif.) was used to spot the immobilization probes described above onto amino-derivatised glass slides according to the array format in FIG. 3A. The center-to-center distance between two adjacent spots was 350 um. After spotting, the slides were incubated at 80° C. for one hour. Then Stratalinker set for 250 mJ was used to crosslink nucleic acid molecules spotted on the slide surface to immobilize them. In FIG. 3A, the immobilization probes for AP1 were spotted on A1-A5; the immobilization probes for NFkB were spotted on B1-B5; the immobilization probes for Sp1 were spotted on C1-C5; the immobilization probes for TFIID were spotted on D1-D5; the immobilization probes for NC were spotted on E1-E5; and the immobilization probes for HC were spotted on F1-F5. A6, B6, C6, D6, E6 and F6 were spotted with control which was a fluorescent dye-labeled nucleic acid molecule. After spotting, the slide was scanned to detect the control to show that spotting procedures were proper.

C. Preparation of nucleic acid-protein binding system: Three transcription factors (0.1 ug AP1, 300 ng NFkB and 1.0 ug Sp1) and protein capture probes (annealed product of LP and FP) were mixed. General binding buffer was added to reach a final concentration of 1×. The reaction mixture was incubated at room temperature for 30 min. The competitor probe was added into the reaction in experiments shown in FIGS. 3C, 3D, and 3E.

D. Isolation of nucleic acid-protein binding complex: Two percent agarose gel and TBE electrophoresis buffer were prepared and cooled to 4° C. The reaction mixture described above was loaded into the sample well of the agarose gel. The electrophoresis was run under 120V for 20 min. The relevant gel slices were cut out based the position of bromphenol blue.

E. Extraction of nucleic acid: Nucleic acid was collected from the gel slices by using the QIAEX II gel purification kit according to manufacture's instructions.

Figures 3D, 3E:
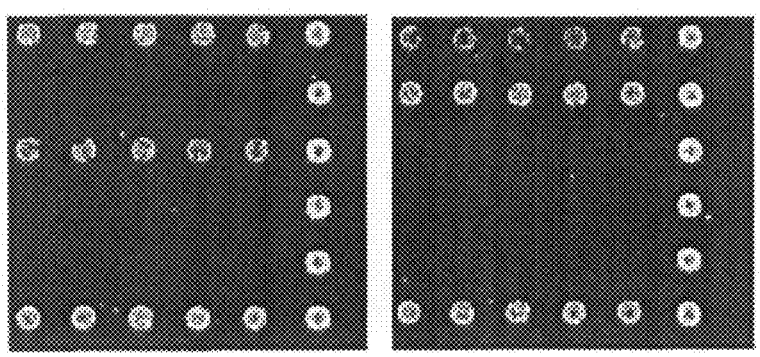
FIG. 3D shows the experimental results of simultaneous detection of three nucleic acid binding proteins in Example 1, in which a competitor NFkB binding probe was added.
FIG. 3E shows the experimental results of simultaneous detection of three nucleic acid binding proteins in Example 1, in which a competitor Sp1 binding probe was added.

F. Hybridization analysis with biochip: The nucleic acid obtained in the previous step was mixed with hybridization buffer (containing HC-LP probe) to make into 15 ml. The hybridization buffer contained 3×SSC and 0.1% SDS. The hybridization mixture was incubated with the slide at 65° C. for 1 hour. The slide was washed with washing buffer containing 0.2×SSC and 0.1% SDS at room temperature for 10 min. The slide was dried by spinning at 1000 rpm. Then the slide was blocked with 1% BSA at 37° C. for 30 min. The slide was washed with PBST at room temperature for 10 min, and was then dried by spinning at 1000 rpm. A 15 ul solution containing 1 ug/ml Cy3 labeled streptavidin was added to the surface of the slide, and was allowed to react for 1 hr at 37° C. The slide was washed with PBST at room temperature for 10 min. The slide was dried by spinning at 1000 rpm. The slide was scanned by scanarray 4000 image scanner, and the image was analyzed using GenePix. FIG. 3A shows the array format. FIG. 3B shows the results of simultaneous detection of 3 nucleic acid binding proteins on a slide using "end-label method". FIG. 3C shows the results of simultaneous detection of 3 nucleic acid binding proteins on a slide using "end-label method" with competitor probe for nucleic acid binding protein AP1 added into the reaction system. FIG. 3D shows the results of simultaneous detection of 3 nucleic acid binding proteins on a slide using "end-label method" with competitor probe for nucleic acid binding protein NFkB added into the reaction system. FIG. 3E shows the results of simultaneous detection of 3 nucleic acid binding proteins on a slide using "end-label method" with competitor probe for nucleic acid binding protein Sp1 added into the reaction system. The results show that the "end-label method" of the present invention can easily detect 3 transcription factors. Because the sequence in NC is from promoter of prokaryotic phage and differs significantly from eukaryotic transcription factor binding sequence, and thus, cannot bind to any transcription factors described above. Thus, the signal from NC probe was always negative. HC was used as a hybridization control. HC was added before hybridization and was used to normalize between different spotting format. Accordingly, the HC signal is always positive.

Example 2

Using DNA Biochip to Simultaneously Detect Three Nucleic Acid Binding Proteins AP1, NFkB and Sp1 (Single Strand Amplification)

Figure 4:
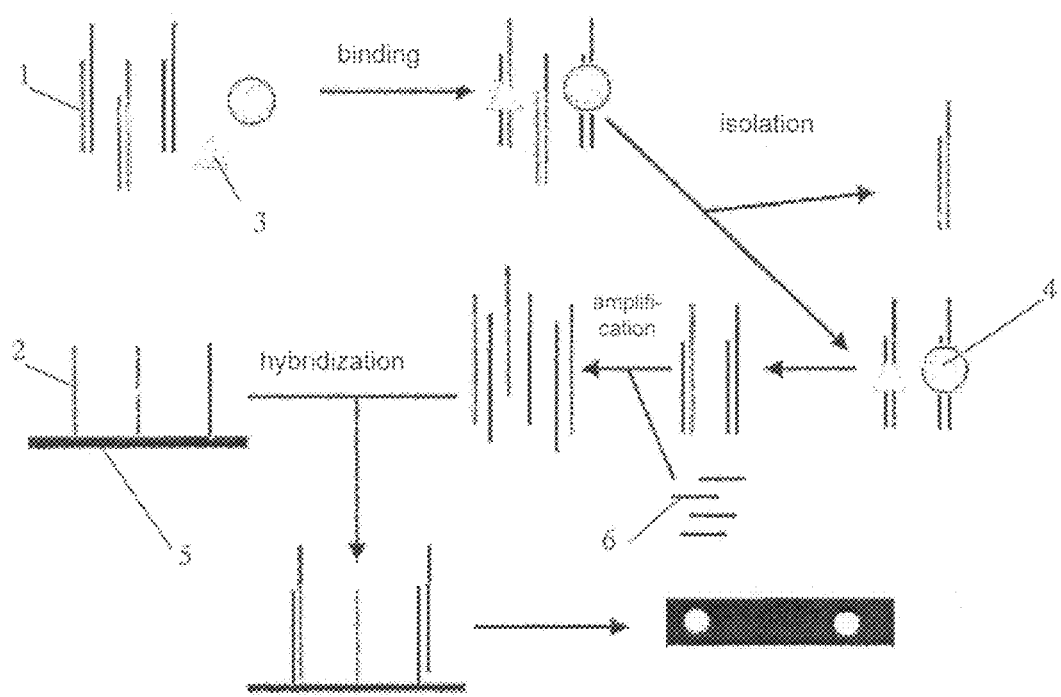
FIG. 4 shows an operation diagram of detection of multiple nucleic acid binding proteins with "single-strand amplification method" used in the present invention.

FIG. 4 shows an operation diagram of detection using single strand amplification method. Capture probes 1 were mixed with target protein 3 (represented by the circle and the triangle in the Figure). The capture probe-nucleic acid binding protein complexes 4 formed were isolated and the capture probes were collected. Primer 6 was used to amplify the capture probes collected, and the amplified product was hybridized with immobilization probes 2 immobilized on biochip 5. The hybridization signal was detected to obtain the result.

Figure 5:
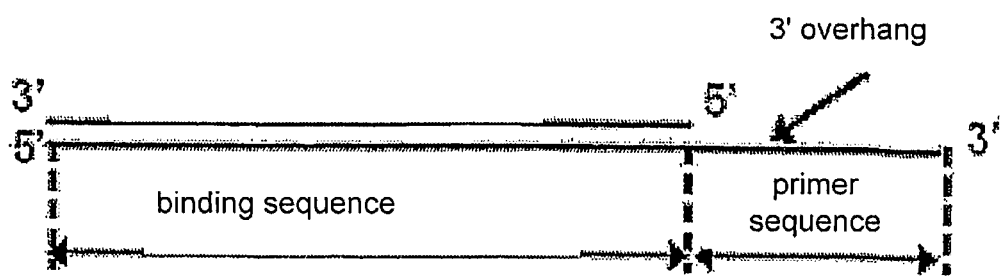
FIG. 5 shows a diagram of probe and primer designs for detecting multiple nucleic acid binding proteins with "single-strand amplification method" used in the present invention/
Figure 5:
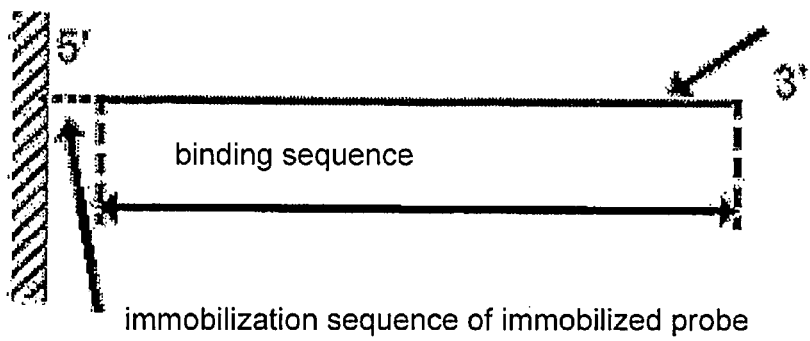

FIG. 5 shows a preferred design for capture probes, immobilization probes and primers. The double stranded capture probe contains a sequence that a nucleic acid binding protein binds, and one strand contains a 3' overhang. The primer sequence is complementary to the 3' overhand. The sequence of the immobilization probe is consistent with the binding sequence.

Materials:

Transcription factors AP-1(c-Jun) (#E3061), NFkB(p50) (#E3770) and Sp1 (#E6391) were obtained from Promega (Madison, Wis.). The general binding buffer contained 10 mM Tris-HCl (pH 7.5), 4% glycerol, 1 mM MgCl2, 0.5 mM EDTA, 5 mM DTT, 50 mM NaCl, and 0.05 mg/ml poly

TABLE 1

Sequences of immobilization probes and capture probes for several transcription factors (TF)

| Group | TF | Probe No. | Probe Name | Probe Sequence |
|---|---|---|---|---|
| 1 | AP-1 | 1 | AP-1-IP | 5'-$T_{20}$-CGCTTGATGAGTCAGCCGGA-TCCCG-3' |
| | | 2 | AP-1-LP | 5'-biotin-CGGGA-TCCGCTGACTCATCAAGCG-3' |
| | | 3 | AP-1-FP | 5'-CGCTTGATGAGTCAGCCGGA-3' |
| | | 4 | AP-1-CP | 5'-TCCGGCTGACTCATCAAGCG-3' |
| 2 | NFκB | 5 | NFκB-IP | 5'-$T_{20}$-AGTTGAGGGGACTTTCCCAGGA-TCCCG-3' |
| | | 6 | NFκB-LP | 5'-biotin-CGGGA-TCCTGGGAAAGTCCCCTCAACT-3' |
| | | 7 | NFκB-FP | 5'-AGTTGAGGGGACTTTCCCAGGA-3' |
| | | 8 | NFκB-CP | 5'-TCCTGGGAAAGTCCCCTCAACT-3' |
| 3 | SP1 | 9 | SP1-IP | 5'-$T_{20}$-AAAGCCCCGCCCCGATATAAT-TCCCG-3' |
| | | 10 | SP1-LP | 5'-biotin-CGGGA-ATTATATCGGGGCGGGGCTTT-3' |
| | | 11 | SP1-FP | 5'-AAAGCCCCGCCCCGATATAAT-3' |
| | | 12 | SP1-CP | 5'-ATTATATCGGGGCGGGGCTTT-3' |
| 4 | TFIID | 13 | TFIID-IP | 5'-$T_{20}$-CGCCTACCTCATTTTATATGCTCTGC-TCCCG-3' |
| | | 14 | TFIID-LP | 5'-biotin-CGGGA-GCAGAGCATATAAAATGAGGTAGGCG-3' |
| | | 15 | TFIID-FP | 5'-CGCCTACCTCATTTTATATGCTCTGC-3' |
| | | 16 | TFIID-CP | 5'-GCAGAGCATATAAAATGAGGTAGGCG-3' |
| 5 | NC | 17 | NC-IP | 5'-$T_{20}$-CTATGTGGTGAACTCCTCCTAAATA-TCCCG-3' |
| | | 18 | NC-LP | 5'-biotin-CGGGA-CGGGATATTTAGGAGGAGTTCACCACATAG-3' |
| | | 19 | NC-FP | 5'-CTATGTGGTGAACTCCTCCTAAATA-3' |
| 6 | HC | 20 | HC-IP | 5'-$T_{20}$-AGACGGAAGACATATGGCCGCTC-TCCCG-3' |
| | | 21 | HC-LP | 5'-biotin-CGGGA-GAGCGGCCATATGTCTTCCGTCT-3' |

(dl-dC)·(dl-dC). The electrophoresis buffer was 0.5×TBE (0.9 M Tris, 0.9 M boric acid and 0.02 M EDTA, pH 8.0). Washing buffer was PBST (PBS, and 0.1% Tween 20). The agarose for electrophoresis was obtained from Biowest (Miami, Fla.). Bovine serum albumin (BSA) was obtained from Amresco (Solon, Ohio). The Cy3-labeled streptavidin was obtained from Amersham Biosciences (Uppsala, Sweden).

Experimental Procedures:

A. Preparation of DNA probes: All the probes were synthesized by Bioasia Inc. (Shanghai, China) and their sequences are listed in Table 2. In each group of probes, LFP and LP' formed the capture probe for the corresponding transcription factor; and IP probe was the immobilization probe. The preparation of the immobilization probe in each group is the same as "Preparation of DNA probes" in Example 1. Protein capture probes were dissolved in water, and were allowed to anneal with corresponding probes (LFP and LP' probes in each group) to form double stranded DNA. The final concentration for each probe group was 60 nM.

B. Preparation of DNA chip: The procedures are the same as "Preparation of DNA chip" in Example 1.

C. Preparation of nucleic acid-protein binding system: Three transcription factors (0.1 ug Ap1, 100 ng NFkB and 0.1 ug Sp1) and protein capture probes were mixed. General binding buffer was added to reach a final concentration of 1×. The binding reaction occurred at room temperature for 30 min.

D. Isolation of nucleic acid-protein binding complex: Two percent agarose gel and TBS electrophoresis buffer were prepared and cooled to 4° C. The reaction mixture described above was loaded into the sample well of the agarose gel. The electrophoresis was run under 120 V for 20 min. The relevant gel slices were cut out based on the position of bromphenol blue.

E. Extraction of nucleic acid: Nucleic acid was collected from the gel slices using the QIAEX II gel purification kit according to manufacture's instructions. Elutions buffer of 20 ul was used to elute.

F. Hybridization analysis with DNA chip: The extracted DNA was vacuum dried, and then re-dissolved in 5 ul water. dNTP, PCR buffer, and Cy3-labeled T7 Pro primer were added for nucleic acid amplification. The PCR cycle was 95° C. for 5 min, 95° C. for 30 sec, 53° C. for 30 sec, 72° C. for 20 sec, with 40 amplification cycles; and 73° C. for 7 min. The amplified product was vacuum dried, and then redissolved in 5 ul water. The dissolved amplified product was made into a 15 ul hybridization solution (with HC-LP probes added into the hybridization solution) containing 3×SSC and 0.1% SDS. The hybridization solution was added to DNA chip to allow hybridization for 1 hour at 65° C. Then, washing buffer containing 0.2×SSC and 0.1% SDS was used to wash the slide for 10 min at room temperature. The slide was dried by spinning at 1000 rpm. Scanarray 4000 image scanner was used to scan the slide, and the image was analyzed using GenePix.

The "end-label method" described in Example 1 was used to detect the three transcription proteins in this example and was used as a control for result comparison.

Figures 6A, 6B:
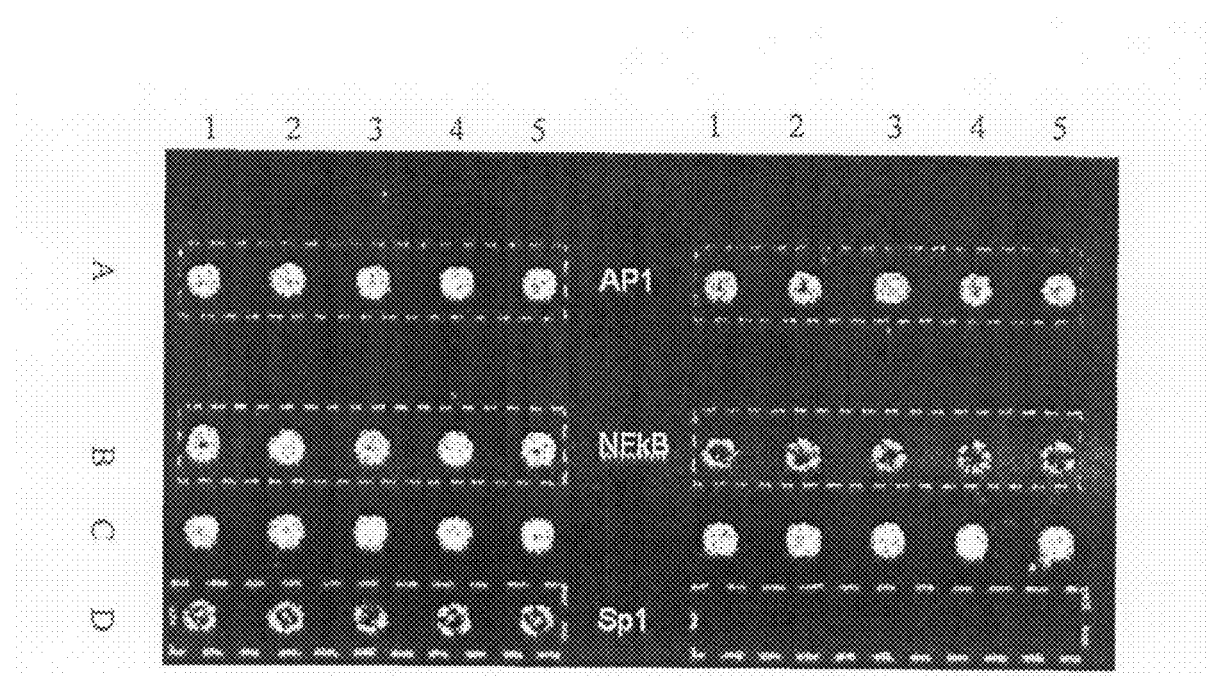
FIG. 6A shows the experimental results of simultaneous detection of three nucleic acid binding proteins (AP1, NFkB and Sp1) with "single-strand amplification method" in Example 2.
FIG. 6B shows the experimental results in Example 2, using the "end labeling method" described in Example 1.
Figure 7:
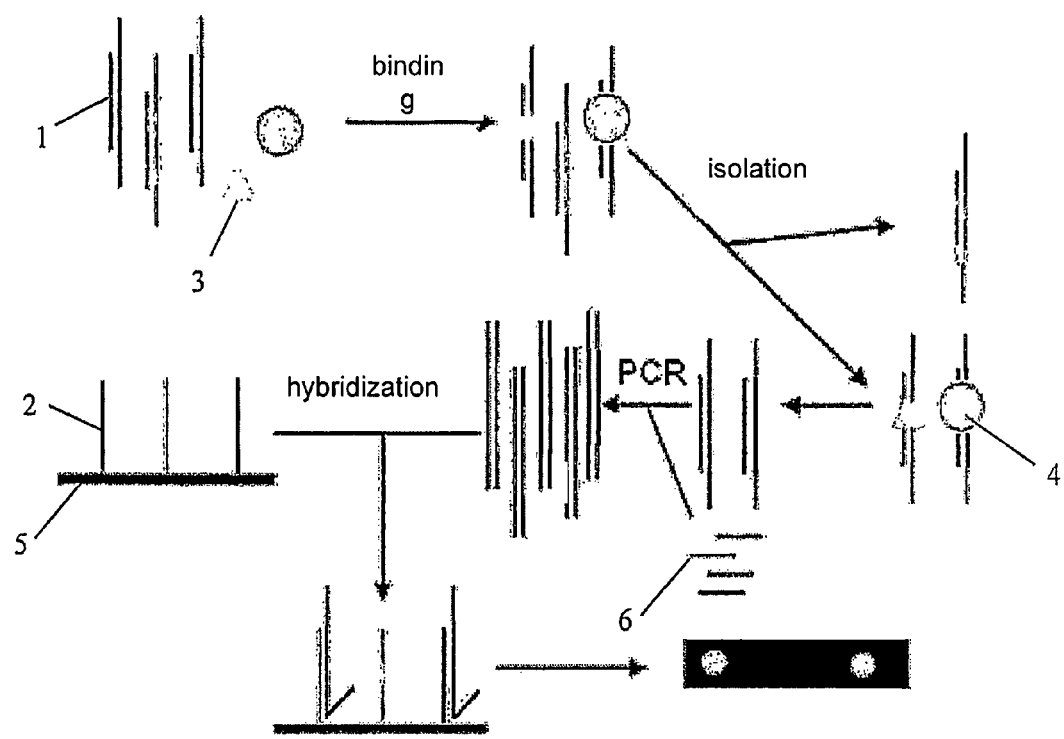
FIG. 7 shows an operation diagram of detection of multiple nucleic acid binding proteins with "double-strand amplification method" used in the present invention.
Figure 8:
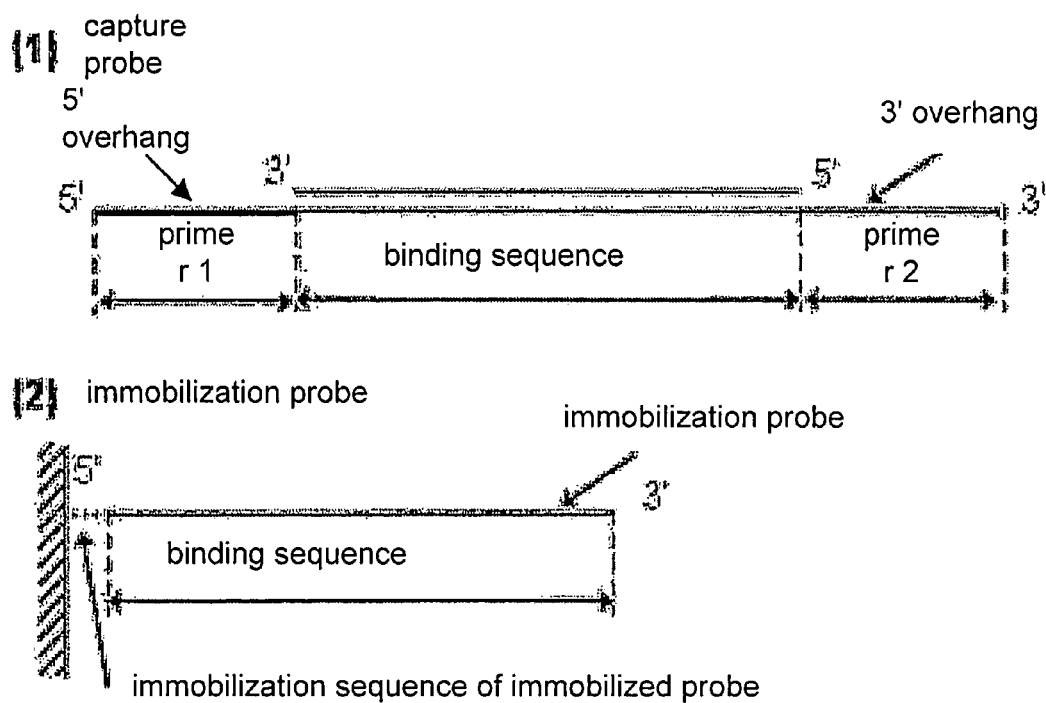
FIG. 8 shows a diagram of probe and primer designs for detecting multiple nucleic acid binding proteins with "double-strand amplification method" used in the present invention.

The results are shown in FIG. 6A and FIG. 6B. FIG. 6A shows the result of the detection with "single strand amplification method". FIG. 6B shows the result of the detection with "end-label method" in Example 1. In this figure, A1-A5 is the result of detection of AP1; B1-B5 is the result of detection of NFkB; C1-C5 is the hybridization control (HC; see Table 1 for sequence of HC-IP and HC-LP); D1-D5 is the result of detection of Sp1. These results indicated that the sensitivity of detection was enhanced using single strand amplification method; signals undetectable using end-label method were detected with single primer amplification.

TABLE 2

Sequences of probes with 3' overhang

| Group | TF | Probe No. | Probe Name | Probe Sequence |
|---|---|---|---|---|
| 1 | AP-1 | 1 | AP-1-IP | 5'-T$_{20}$-CGCTTGA<u>TGAGTCAG</u>CCGGA-TCCCG-3' |
|  |  | 22 | AP-1-LFP | 5'-CGCTTGA<u>TGAGTCAG</u>CCGGA-*CCCTATAGTGAGTCGTATTACCCC*-3' |
|  |  | 26 | AP-1-LP' | 5'-*CGGGA*-TCCGG<u>CTGACTCAT</u>CAAGCG-3' |
| 2 | NFκB | 5 | NFκB-IP | 5'-T$_{20}$-AGTTGAG<u>GGGACTTTCC</u>CAGGA-TCCCG-3' |
|  |  | 23 | NFκB-LFP | 5'-AGTTGAG<u>GGGACTTTCC</u>CAGGA-*CCCTATAGTGAGTCGTATTACCCC*-3' |
|  |  | 27 | NFκB-LP' | 5'-*CGGGA*-TCCTGG<u>GAAAGTCCCC</u>TCAACT-3' |
| 3 | SP1 | 9 | SP1-IP | 5'-T$_{20}$-AAAGC<u>CCCGCCCC</u>GATATAAT-TCCCG-3' |
|  |  | 24 | SP1-LFP | 5'-AAAGC<u>CCCGCCCC</u>GATATAAT-*CCCTATAGTGAGTCGTATTACCCC*-3' |
|  |  | 28 | SP1-LP' | 5'-*CGGGA*-ATTATATC<u>GGGGCGGG</u>GCTTT-3' |
| 4 |  | 25 | T7 Pro | 5'-Cy3-*GGGGTAATACGACTCACTATAGGG*-3' |

INDUSTRIAL USE

The present invention uses biochip method to detect nucleic acid binding proteins, especially transcription factors. The method includes detection of hybridization signals between the capture probe and immobilization probe. It is a highly sensitive and a high-throughput method. In addition, when the two improved methods of the present invention (single strand amplification before hybridization, double strand amplification before hybridization) and the primer can be pre-labeled, there is no need to label each group of capture probes. The experimental cost can be significantly reduced.

The present method can be widely used for disease diagnosis, drug target screening, and study of disease process.

---

The invention claimed is:

1. A biochip based method for detecting nucleic acid binding proteins, comprising:
   1) adding a solution containing several groups of nucleic acid capture probes to a biological sample containing target nucleic acid binding proteins, whereby complexes between the nucleic acid capture probes and the nucleic acid binding proteins are formed, wherein the nucleic acid capture probes contain at least a sequence that target nucleic acid binding proteins can bind, and wherein one strand of the nucleic acid capture probes in each group contains a 3' overhang;
   2) isolating the nucleic acid capture probe-nucleic acid binding protein complexes and collecting the nucleic acid capture probes in the complexes;
   3) amplifying the collected nucleic acid capture probes by single-stranded PCR amplification using one primer, wherein the primer can hybridize to the 3' overhang sequence of the nucleic acid capture probes;
   4) hybridizing the amplified capture probes in step 3) with single stranded immobilization probes immobilized on the substrate of a biochip, wherein the immobilization probes contain a sequence complementary to the corresponding nucleic acid capture probes or one strand of the nucleic acid capture probes; and
   5) detecting the hybridization result.

2. The method of claim 1, wherein the isolation of the nucleic acid capture probe-nucleic acid binding protein complexes in step 2) is a process of gel electrophoresis of the mixture sample from step 1), cutting gel slices, and recovering with gel purification kit or electro-elution method to obtain the isolated nucleic acid capture probe-nucleic acid binding protein complexes.

3. The method of claim 1, wherein the nucleic acid binding proteins are double-stranded DNA (dsDNA) binding proteins, RNA binding proteins, or single-stranded DNA (ss-DNA) binding proteins.

4. The method of claim 3, wherein the dsDNA binding proteins are transcription factors.

5. The method of claim 1, wherein the nucleic acid capture probes contains a nucleic acid sequence that can be bound by nucleic acid binding proteins.

6. Rewrite as The method of claim 5, wherein each immobilization probe is complementary to the 3' overhang sequence of its corresponding nucleic acid capture probe.

7. The method of claim 1, wherein the 3' overhang sequence in each group of the nucleic acid capture probes having the 3' overhang is identical, and the primer sequence is completely complementary to the 3' overhang sequence.

8. Rewrite as The method of claim 7, wherein the primer is labeled with a labeling molecule.

9. The method of claim 8, wherein the 5' end of the primer is labeled.

10. The method of claim 9, wherein the labeling molecule is a biotin, a digoxin, a fluorescence dye, a quantum dye, a gold particle, or a nano-particle.

11. The method of claim 1, wherein the isolation of the nucleic acid capture probe-nucleic acid binding protein complexes in step 2) is chromatographying the mixture sample from step 1) to obtain the isolated nucleic acid capture probe-nucleic acid binding protein complexes.

12. The method of claim 1, wherein the isolation of the nucleic acid capture probe-nucleic acid binding protein complexes in step 2) is filtering the mixture sample from step 1) with a membrane capable of adsorbing proteins to obtain the isolated nucleic acid capture probe-nucleic acid binding protein complexes.

13. The method of claim 1, wherein the isolation of the nucleic acid capture probe-nucleic acid binding protein complexes in step 2) is a process of adding antibodies specifically recognizing each nucleic acid binding protein to the mixture sample from step 1) and isolating antibodies to obtain the isolated nucleic acid capture probe-nucleic acid binding protein complexes.

14. The method of claim 1, wherein the isolation of the nucleic acid capture probe-nucleic acid binding protein complexes in step 2) is a process of separating the mixture sample from step 1) by capillary electrophoresis and collecting the nucleic acid capture probe- nucleic acid binding protein complexes.

15. The method of claim 6, wherein the overhang of the nucleic acid capture probes is labeled with a labeling molecule.

16. The method of claim 15, wherein the labeling molecule is a biotin, a digoxin, a fluorescence dye, a quantum dye, a gold particle, or a nano-particle.

17. The method of claim 7, wherein nucleotides labeled with a labeling molecule are added into the amplification process when using the primer for amplification.

18. The method of claim 17, wherein the labeling molecule is a biotin, a digoxin, a fluorescence dye, a quantum dye, a gold particle, or a nano-particle.

19. The method of claim 1, wherein one strand of the capture probes in each group contains a 3' overhang and a 5' overhang, and wherein the amplification process is performed with two primers, wherein one primer can hybridize to the 3' overhang sequence of the nucleic acid capture probes containing the 3' overhang and the 5' overhang, and the other primer contains a sequence identical to the 5' overhang sequence of the nucleic acid capture probes containing the 3' overhang and the 5' overhang.

20. The method of claim 19, wherein the 3' overhang sequence in each nucleic acid capture probe containing the 3' overhang and the 5' overhang is identical; and the 5' overhang sequence in each nucleic acid capture probe containing the 3' overhang and the 5' overhang is identical, wherein one primer can hybridize to the 3' overhang sequence of the nucleic acid capture probes containing the 3' overhang and the 5' overhang, and the other primer contains a sequence identical to the 5' overhang sequence of the nucleic acid capture probes containing the 3' overhang and the 5' overhang.

21. The method of claim 20, wherein the primers are labeled with a labeling molecule when the two primers are used for amplification.

22. The method of claim 21, wherein the 5' end of the primers is labeled.

23. The method of claim 22, wherein the labeling molecule is a biotin, a digoxin, a fluorescence dye, a quantum dye, a gold particle, or a nano-particle.

24. The method of claim 20, wherein nucleotides labeled with a labeling molecule are added into the amplification process when using the two primers for amplification.

25. The method of claim 24, wherein the labeling molecule is a biotin, a digoxin, a fluorescence dye, a quantum dye, a gold particle, or a nano-particle.

* * * * *